United States Patent [19]

Deindoerfer

[11] 4,238,449

[45] Dec. 9, 1980

[54] REAGENT HOLDER

[75] Inventor: Fred H. Deindoerfer, Northridge, Calif.

[73] Assignee: International Diagnostic Technology, Inc., Santa Clara, Calif.

[21] Appl. No.: 40,592

[22] Filed: May 21, 1979

[51] Int. Cl.³ .................. G01N 21/33; G01N 33/48
[52] U.S. Cl. .......................... 422/58; 23/915;
 250/461 R; 356/246; 422/104
[58] Field of Search ............ 23/230 B, 915; 422/58,
 422/68, 104; 250/302, 373, 461 R; 356/246

[56] References Cited

U.S. PATENT DOCUMENTS

| 3,999,948 | 12/1976 | Deindoerfer et al. | 23/230 B |
|---|---|---|---|
| 4,144,452 | 3/1979 | Harte | 250/373 |

Primary Examiner—R. E. Serwin
Attorney, Agent, or Firm—Limbach, Limbach & Sutton

[57] ABSTRACT

A reagent holder for fluoro immunoassays with two examination surfaces on opposite sides and a resiliently deformable detent operable to retain the reagent holder in an examination location regardless of which side is being examined.

1 Claim, 6 Drawing Figures

U.S. Patent  Dec. 9, 1980  4,238,449
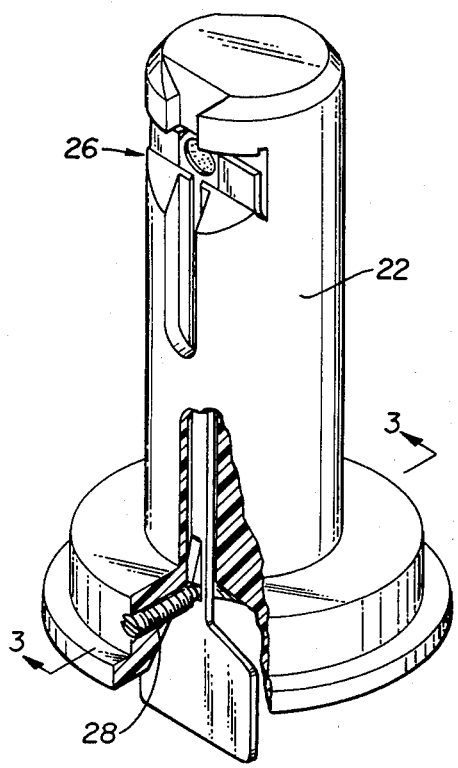
FIG._1.
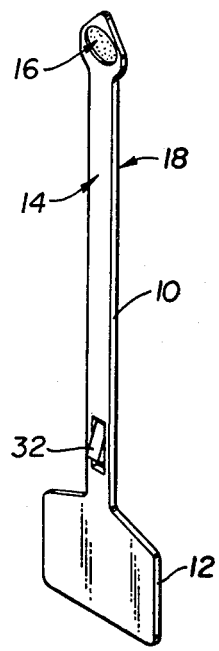
FIG._2A.
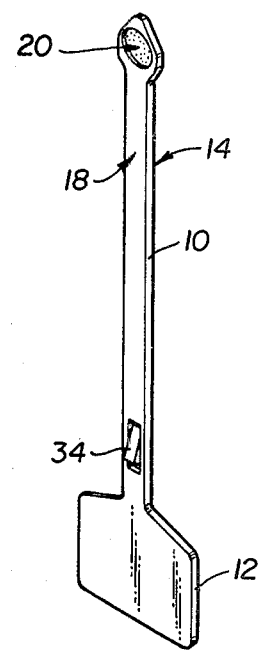
FIG._2B.
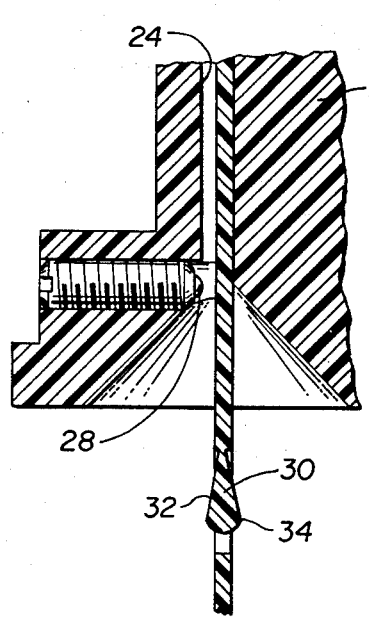
FIG._3A.
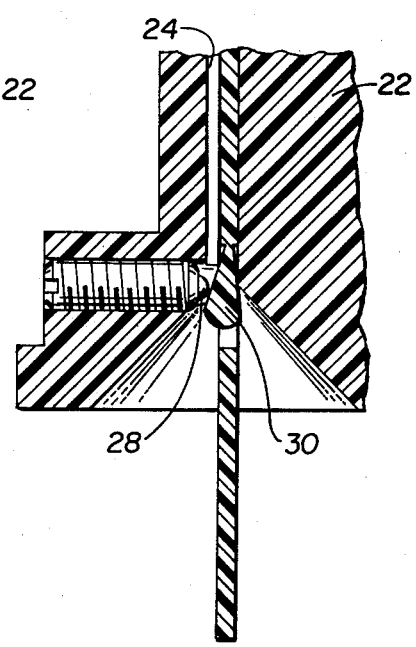
FIG._3B.
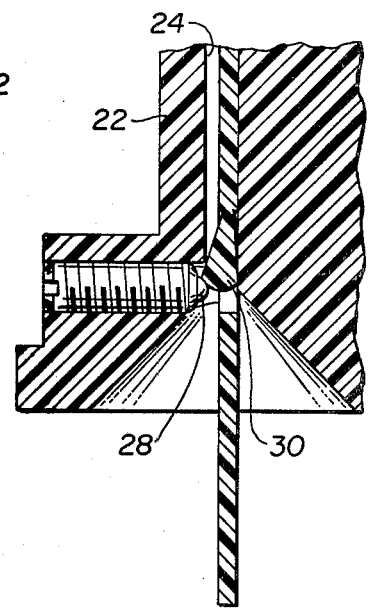
FIG._3C.

REAGENT HOLDER

BACKGROUND OF THE INVENTION

A reagent holder is disclosed in U.S.A. Pat. No. 3,999,948 for performing fluoro immunoassays. This reagent holder includes an elongated shaft with an examination surface area at one end where an immunofluorescent sample is supported in an instrument during examination. A preferred form of the reagent holder is shown in FIG. 13 of U.S. Pat. No. 4,144,452 where a cam surface on one side of the reagent holder cooperates with a detent in an examination instrument to retain the reagent holder in an examination location in the fluorometer.

An improved form of fluoro immunoassays has been developed in U.S. Patent Application Ser. No. 943,314 filed Sept. 18, 1978 where two test surfaces are provided on the same reagent holder and accompany each other through an immunoassay procedure. In accordance with this invention, an improved reagent holder is provided for performing the improved method in the equipment which used the original single sided reagent holder.

SUMMARY OF INVENTION

In accordance with this invention a second diagnostic surface area is provided on the back side of the reagent holder in alignment with the first diagnostic surface area and a second cam surface is provided on the opposite side of the shaft of the reagent holder from the first cam surface for retaining the reagent holder in an examination location for examination of the second diagnostic surface area. In the operation of the fluorometer, it is important to have the shaft of the reagent holder substantially fill the passageway by which the reagent holder is inserted into its receiver to exclude ambient light and atmosphere, and for this reason it is desirable to have one side of the passageway receive the reagent holder flush with the shaft of the reagent holder while the detent engaging the cam surface on the reagent holder engages the opposite side of the shaft. This provides an inherent design problem for construction of a two-sided reagent holder.

In accordance with this invention the shaft of the reagent holder is provided with a flexibly mounted wedge shaped portion with the two cam surfaces on opposite sides thereof so that the wedge shaped portion can flex to permit each of the cam surfaces to be inclined to the length of the shaft in an operative position while the other cam surface is generally parallel to the shaft. These and other features of the invention will become apparent from the following description of a preferred embodiment thereof read in conjunction with the attached drawing in which:

FIG. 1 is a perspective view of a receptacle of a photometer in which the reagent holder of this invention is received, FIG. 2A is a perspective view of one side of the reagent holder of FIG. 1, and FIG. 2B is a perspective view of the reverse side of the reagent holder of FIG. 2A, and FIGS. 3A, 3B and 3C are cross-sectional views through the receptacle of FIG. 1 taken along the plane indicated at 3—3 in FIG. 1 showing three progressive stages in the insertion of the reagent holder of FIG. 2 and the receptacle of FIG. 1.

The preferred reagent holder of this invention includes an elongated shaft 10 with a handle portion 12, a front side 14 with a first diagnostic surface area 16 and a back side 18 with a second diagnostic surface area 20. As explained in the above mentioned patents and application, the diagnostic surface area carries a film to which are bound biological materials having fluorescently tagged constituents which may be detected in the fluorometer.

The receptacle shown in FIG. 1 includes a body portion 22 containing a bore 24 which terminates at an examination position 26 dimensioned to snugly receive the reagent holder with either the first diagnostic area 16 or the second diagnostic area 20 positioned at the examination position 26. Mounted in the body 22 is a spring loaded detent 28 which is adapted to receive and retain a cam surface on the reagent holder.

Thus, the reagent holder includes a central wedge shaped portion 30 best seen in FIG. 3A which has a first cam surface 32 on one side and a second cam surface 34 on the other side and the wedge shaped portion 30 is flexibly formed with the shaft 10 so that it may bend out of the way during insertion of the reagent holder as shown in FIGS. 3B and 3C. In this way the retainer 28 operates with the two different cam surfaces 32 and 34 when the reagent holder is inserted into the receiver in its two opposite positions.

I claim:

1. In an elongated diagnostic reagent holder having front and rear sides, an elongated shaft, a diagnostic surface area on the front side of the holder near one end of the shaft for supporting an immunofluorescent sample, and a cam surface on one side of the shaft adapted to engage a retainer in a receiver for the reagent holder to retain the reagent holder at an examination position in the receiver, the improved reagent holder having,
   a. a second diagnostic surface area on the back side of the holder opposite to the first diagnostic surface area for supporting a second immunofluorescent sample, and
   b. a second cam surface on the second side of the shaft opposite to the first cam surface for retaining the reagent holder at the examination position during examination of the second diagnostic surface area with the shaft having a flexibly mounted wedge shaped portion thereof with the first and second cam surfaces on opposite sides thereof whereby each of the cam surfaces may be inclined to the length of the shaft while the other cam surface is generally parallel to the shaft.

* * * * *